US005362907A

United States Patent [19]
Laue et al.

[11] Patent Number: 5,362,907
[45] Date of Patent: Nov. 8, 1994

[54] INTERMEDIATES AND THEIR USE IN THE PREPARATION OF S-KETOPROFEN

[75] Inventors: Christian Laue, Langenfeld; Georg Schröder, Leverkusen; Dieter Arlt, Köln, all of Germany

[73] Assignee: Bayer Aktiengesellschaft, Leverkusen, Germany

[21] Appl. No.: 934,044

[22] Filed: Aug. 21, 1992

[30] Foreign Application Priority Data

Aug. 30, 1991 [DE] Germany ............................ 4128787

[51] Int. Cl.$^5$ ............................................. C07C 59/48
[52] U.S. Cl. ................................................... 562/470
[58] Field of Search ......................................... 562/470

[56] References Cited

U.S. PATENT DOCUMENTS

| 3,641,127 | 2/1972 | Farge et al. | 260/516 |
| 4,304,931 | 12/1981 | Nicholson et al. | 562/469 |
| 4,962,124 | 10/1990 | Sunshine et al. | 514/568 |
| 4,983,765 | 1/1991 | Lukas et al. | 562/401 |
| 5,097,064 | 3/1992 | Grosselin | 562/401 |

FOREIGN PATENT DOCUMENTS

| 0245959 | 4/1987 | European Pat. Off. |
| 0272787 | 11/1987 | European Pat. Off. |
| 0366390 | 10/1989 | European Pat. Off. |
| 0369691 | 11/1989 | European Pat. Off. |
| 0379917 | 1/1990 | European Pat. Off. |
| 0398132 | 5/1990 | European Pat. Off. |
| 0403188 | 6/1990 | European Pat. Off. |

OTHER PUBLICATIONS

CA 116(7): 59373r 1 Aug. 1991.
Tetrahedron Report No. 205, vol. 42, No. 15, pp. 4095–4131, 1986.
Giovanni Comisso, "Enantioselective Synthesis and Absolute Configuration of (+)-α-(3-Benzoylphenyl)-Propionic Acid," in *Gazetta Chimica Italiana*, 1980, pp. 123–127.
Gian Paolo Chiusoli, "Palladium–Catalyzed Carbonylation of Alkynes. II*. Aspects of Additive, Oxidative, and Reductive Carbonylation (*)," in *Gazetta Chimica Italiana*, 1985, pp. 691–696.
A. Abas, "Enantioselective Disposition of 2-Arylpropionic Acid Nonsteroidal Anti–Inflammatory Drugs. IV. Ketoprofen Disposition," in The *Journal of Pharm. and Exp. Ther.*, Oct. 24, 1986, pp. 637–641.
Kazushi Mashima, et al., "Synthesis and Characterization of Cationic Trinuclear BINAP-Ru(II) Complexes: Crystal Structure of [Ru3Cl5((S)-binap)3]BF4" in *Tet. Letters*, 1991, pp. 3101–3104.
Andrew Pelter, et al., "Asymmetric Synthesis of Homochiral Dibenzylbutyrolactone Lignans by Conjugate Addition to a Chiral Butenolide," in *Tetrahedron: Asymmetry*, 1990, pp. 857–860.
Chemistry Letters, 1990, pp. 523–526.
Tamejiro Hiyama, "A Facile, Practical Synthesis of 2-(6-Methoxy-2-naphthyl)priopenoic Acid," 1990, pp. 640–642.
E. R. Jones, et al., "Researches on Acetylenic Compounds. Part XXII. The Reaction Between Nickel Carbonyl and Monosubstituted Acetylenic Compounds," 1950, pp. 230–236.
C. W. Baird, "Synthesis of Organic Compounds by Direct Carbonylation Reactions using Metal Carbonyls," 1962, pp. 283–302.
P. F. Holt, et al., "Polycyclic Cinnoline Derivatives. Part VII. Benzo[c][$^{15}$N]cinnoline," *J. Chem. Soc.*, 1961, pp. 1404–1407.
Boris G. Zupancic, et al., "Catalytic Activity of Polyethylene Glycols in the Reduction of Carbonyl Compounds under Phase–Transfer Catalyzed Condition," in *Synthetic Communications*, 1982, pp. 881–886.

*Primary Examiner*—Paul J. Killos
*Attorney, Agent, or Firm*—Sprung Horn Kramer & Woods

[57] ABSTRACT

The present invention relates to novel 2-arylpropenoic acids, derivatives thereof, processes for their preparation and their use in the preparation of S-ketoprofen.

7 Claims, No Drawings

INTERMEDIATES AND THEIR USE IN THE PREPARATION OF S-KETOPROFEN

The present invention relates to novel 2-aryl-propenoic acids, derivatives thereof, processes for their preparation and their use in the preparation of S-ketoprofen Racemic ketoprofen is a known analgesic and antipyretic.

As with other arylpropenoic acids, such as, for example, Naproxen and Ibuprofen it is known that the S-enantiomer has specific advantages compared to the racemate, such as halving the effective dose and accelerating the onset of effect (compare EP-A 4,962,124).

Whereas numerous synthesis routes are known for racemic arylpropionic acids and also for racemic ketoprofen (compare, for example, J. P. Rieu et al, Tetrahedron, 42, 4095 (1986)), enantiomerically pure (S)-ketoprofen can only be prepared with difficulty, in small amounts and with poor yields. It has, for example, been proposed to carry out an optical resolution of 2-(3-benzylphenyl)propionic acid with subsequent oxidation to give (S)-ketoprofen (G. Comisso et al., Gazz. Chim, Italy 110, 123 (1980)). The yield given there of 16% is already very low. In a repetition of this process, only even poorer yields could be achieved.

In U.S. Pat. No. 3,641,127, optical resolution of 2-(2-thiaxanthonyl)-propionic acids with subsequent multistage conversion to (S)-ketoprofen is proposed. The total yields attainable in this case are even substantially poorer than those in the abovementioned process of G. Comisso.

By a chromatographic diastereomeric separation of the amides of ketoprofen using chiral amines, only mg amounts of (S)-ketoprofen can be obtained following hydrolysis of the amides (compare Abas et al., J. Pharmacol. Exp. Ther. 240, 637 (1987)). The optical resolution described in DE-A 3 824 353 using phenethylamine was also attempted, but without success.

As a further possibility, the asymmetric hydrogenation of dehydroketoprofen using chiral rhodium catalysts has been suggested. However, these hydrogenations show a poor enantioselectivity. In the abovementioned publication by G. Comisso, an enantioselectivity of, for example, 60% enantiomeric excess (subsequently termed e.e.) is given. Even when hydrogenation is carried out in 2-phase systems as described in EP-A 419 312, enantioselectivities of only 71% e.e. result. A significant disadvantage of the asymmetric hydrogenations mentioned there is their difficult large-scale execution, which can only be carried out at great expense. Furthermore, the chiral catalysts to be used can be prepared only with extreme difficulty.

In summary, it can be stated that hitherto no technical process is known which permits the production of relatively large amounts of (S)-ketoprofen.

The invention relates to novel (2)-arylpropenoic acids of the general formula (II)

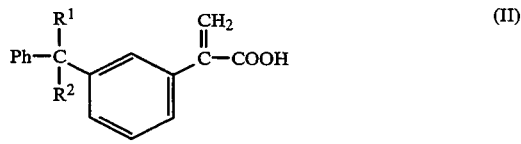

in which

the group is a group which can be converted into a keto group, in particular $R^1$ and $R^2$ are identical or different and in each case represent hydrogen, hydroxyl, alkoxy having up to 10 C atoms, cycloalkoxy having 5 to 10 C-atoms, aralkoxy having 7 to 12 C atoms or aryloxy having 6 to 10 C atoms, which is unsubstituted or substituted by alkyl or alkoxy having in each case 1 to 5 C atoms, or represent the group $O_2CR^3$, where $R^3$ is hydrogen, alkyl having up to 10 C-atoms, cycloalkyl having 5 to 10 C-atoms, aralkyl having 7 to 12 C-atoms or aryl having 6 to 10 C-atoms, unsubstituted or substituted by alkyl or alkoxy having in each case 1 to 5 C-atoms, or represent the group $OSiR^4R^5R^6$, where $R^4$, $R^5$ and $R^6$, independently of each other, each have the meaning given for $R^3$ or represent the group $NR^7R^8$, where $R^7$ and $R^8$, independently of each other, have the meaning given for $R^3$ or represent a 2-tetrahydropyryl group or $R^1$ and $R^2$ together represent a group of the structure

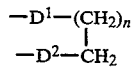

in which $D^1$ and $D^2$, independently of each other, each represent oxygen, sulphur or the group $NR^3$, where $R^3$ has the meaning given above and n represents 1, 2 or 3.

Of particular interest are compounds of the general formula (II) in which $R^1$ and $R^2$ in each case represent hydrogen, hydroxyl, alkoxy having 1 to 4 C-atoms, benzyloxy, acetyloxy, benzoyloxy, tri(alkyl)silyl having in each case 1 to 4 C-atoms in the alkyl radicals, dialkylamino having in each case 1 to 4 C-atoms in the alkyl radicals or 2-tetrahydropyryl or $R^1$ and $R^2$ together represent the group $-O(CH_2)_n-CH_2-D^2-$, where n represents 1, 2 or 3 and $D^2$ represents oxygen or alkylamine having 1 to 4 C-atoms.

Particular preference is given to the following representatives of the compounds of the general formula (II):
the alcohol ($R^1=OH$, $R^2=H$),
the alkyl ether ($R^1=OCH_3$, $OC_2H_5$, $R^2=H$),
dioxo compound ($R^1$ and ($R^2=-O(CH_2)_2O-$ or $-O(CH_2)_3O-$).
the ketal ($R^1$ and $R^2=(-OC_2H_5)_2$),
ester ($R^1=OOCCH_3$, $R^2=H$),
trialkylsiloxyl ether ($R^1=(CH_3)_3SiO$, $R^2=H$).

The invention further relates to the use of the novel compounds of the general formula (II) for the preparation of (S)-ketoprofen, characterised in that the compounds of the general formula (II) are hydrogenated in the presence of a catalyst which comprises a chiral transition metal complex and in the presence or absence of inert organic solvents to give compounds of the general formula (I)

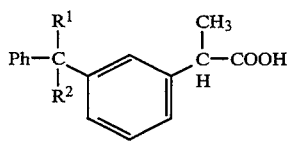

in which
R$^1$ and R$^2$ have the meaning given above, but do not simultaneously represent hydrogen,
and the CR$^1$R$^2$ group is subsequently converted into a keto group by conventional methods.

Chiral transition metal complexes, useable as catalysts, which may be mentioned are, preferably, rhodium complexes, ruthenium complexes and iridium complexes with chiral bisphosphines.

The bisphosphines usable in this case are known or can be prepared by conventional methods (compare EP-A 403 188). The complexes of ruthenium, iridium and rhodium are likewise known or can be prepared by known conventional methods (compare EP-A 369 691, 366 390, 245 959, 398 132 or Tetrahedron Letters 32, 3101 (1991) or Tetrahedron Asymmetry 1, 859 ( 1990 ))

Solvents which can be used for the hydrogenations are lower alcohols such as methanol or ethanol, or toluene, benzene, tetrahydrofuran or their mixtures, preferably methanol; the concentrations are 0.5 to 20 l per mole of starting material.

The catalyst is used in a concentration of 0.05 to 0.0001 mol, preferably in a concentration of 0.01 to 0.001 mol, per mole of arylpropenoic acid.

In the case of the rhodium catalysts, 0.1 to 1.1 equivalents of tertiary amines are particularly preferably added. The hydrogen pressure of the reaction is 1 to 200 atm, preferably 10 to 100 atm, the temperature is 5° to 100° C., preferably 10° to 70° C. and the duration of reaction is 10 min to 52 h.

The hydrogenation is preferably carried out in a degassed inert solvent with exclusion of oxygen and with stirring or shaking.

The invention likewise relates to a plurality of processes for the preparation of compounds of the general formula (II)

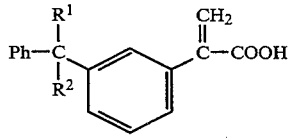

in which
R$^1$ and R$^2$ have the meaning given above, which are characterised in that
A) compounds of the general formula (III)

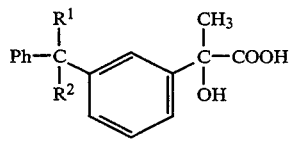

in which

R$^1$ and R$^2$ have the meaning given above, are dehydrated by conventional methods or
B) Compounds of the formula (IV)

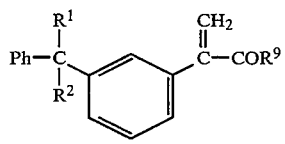

in which
R$^1$ and R$^2$ have the meaning given above and
R$^9$ represents alkoxy having 1 to 10 C-atoms, cycloalkoxy having 5 to 10 C-atoms, aralkoxy having 7 to 12 C-atoms or aryloxy having 6 to 10 C-atoms, which is unsubstituted or substituted by alkyl or alkoxy each having 1 to 5 C-atoms,
are hydrolysed by conventional methods.

Variant A

The elimination of water according to process variant A) is preferably carried out by the action of heat and/or acid in the presence or absence of a solvent at temperatures between 50° and 250° C. preferably between 70° and 150° C, in particular at the boiling point of the solvent used.

The solvents used can preferably be ethers, hydrocarbons, chlorinated hydrocarbons, dimethylformamide, dimethyl sulphoxide or mixtures thereof. The acids used are preferably mineral acids, sulphonic acids or carboxylic acids. Particular preference is given to 5 to 30% strength hydrochloric acid, polyphosphoric acid, 2 to 15% sulphuric acid in dioxane or solutions of 0.1 to 5% p-toluenesulphonic acid in toluene or benzene.

Variant B

The hydrolysis of the compounds of the general formula (IV) according to process variant B) is carried out by conventional methods in the presence or absence of inert organic solvents at temperatures between 20° and 150° C., in particular between 40° and 120° C.

The invention further relates to compounds of the general formula (IV), in which R$^1$, R$^2$ and R$^9$ have the meanings described above, and also to a process for their preparation, characterised in that compounds of the general formula (V)

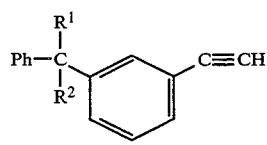

in which
R$^1$ and R$^2$ have the abovementioned meaning, are reacted in the presence of palladium on activated charcoal as catalyst and carbon monoxide at pressures between 1 and 200 bar with an alcohol according to the definition HR$^9$, where R$^9$ has the meaning given above, and with addition of mineral acid, in the presence or absence of an inert aprotic solvent at temperatures between 25° and 160° C.

The literature has already disclosed methods for the preparation of 2-propenoic esters and 2-arylpropenoic acids by reaction of alkines with carbon monoxide in the presence of catalysts (see T. Kusumoto, et al., Chem. Lett., 1990, 523; T. Hiyama, et al., Bull. Chem. Soc. Jpn., 63, 460 (1990)). The catalysts used are palladium black, metal salts or metal salt complexes containing, for example, triaryl phosphines, which must be prepared or which lead to partial reduction, by way of dissolved hydrogen, of the alkines used to give alkenes or which lead to difficulties by separation of the phosphines from the reaction mixture.

Furthermore, the literature discloses reactions of the alkines with stoichiometric amounts of metal carbonyls (see E. R. H. Jones, et al., J. Chem. Soc., 230 (1958); C. W. Bird, Chem. Rev., 283, (1962)), but these do not present any real alternative to the above methods because of the toxicity of the metal carbonyls.

For the reaction of alkines to give the 2-arylpropenoic acids or their esters, heterogeneous catalysts are desired for a simplified application, which catalysts permit a very simple separation of the catalysts from the reaction mixture avoiding all the abovementioned problems. It is known from the literature that palladium on charcoal is an unsuitable catalyst for this reaction (G. P. Giusoli, et al., Gazz. Chim. Ital., 115, 691 (1985)). It was therefore all the more surprising that arylpropenoic acid esters could be prepared in good yields using palladium on charcoal.

The amount of the palladium-charcoal catalyst is preferably 0.1 to 25% by weight, preferably 1 to 20% by weight and in particular 5 to 15% by weight, relative to the compound used of the general formula (V).

The reaction is preferably carried out at pressures between 5 and 150 bar, in particular between 10 and 100 bar.

Particularly suitable alcohols which may be mentioned are lower alcohols having up to 6, in particular having up to 4, C atoms, very particularly methanol and ethanol. The mineral acid is preferably added in amounts of 0.1 to 10 mol, in particular 0.2 to 5 mol, particularly 0.5 to 2 mol, in each case relative to the alkine used of the general formula (V). Particularly preferred mineral acids are hydrogen halides such as hydrobromic, hydrochloric and hydroionic acids.

It has proved advantageous to use 0.1 to 10 mol, preferably 0.2 to 5 mol, particularly 0.5 to 2 mol of alkali metal halides (relative to the alkine used). In addition to chlorides and bromides, iodides are preferred.

The reaction temperature is preferably 40° to 140° C., in particular 50° to 120° C. with reaction times between 1 and 48 hours, in particular between 4 and 24 hours.

The resulting products of the general formula (IV) are purified according to conventional methods such as, for example, chromatography, distillation and crystallisation.

The invention further relates to compounds of the general formula (III)

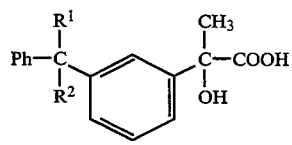

(III)

in which
R$^1$ and R$^2$ have the meaning given above.

The preparation of the compound of the general formula (III) is carried out by reacting Grignard compounds of the general formula (VI)

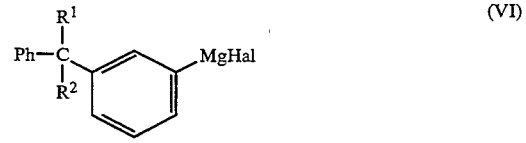

in which
R$^1$ and R$^2$ have the meaning given above and
Hal represents fluorine, chlorine, iodine or bromine, in particular bromine and chlorine,
with a metal pyruvate of the general formula (VII)

Me$^{\oplus \ominus}$OCC—CO—CH$_3$    (VII)

in which
Me represents an alkali metal, an alkaline earth metal (a half equivalent) or MgBr,
in the presence of organic solvents at temperatures between −10° C. and +120° C.

The Grignard compounds of the general formula (VI) to be used as starting compounds are known or can be prepared by known methods (compare DE-A 26 13 817).

The metal salts of pyruvic acid of the general formula (VII) are likewise known and are commercially available. The use of the sodium salt of pyruvic acid is of particular importance. In addition to the metal salts, the corresponding ammonium salts can also be used.

The reaction is preferably carried out by mixing the Grignard compound of the general formula (VI) with compounds of the general formula (VII), which are optionally dissolved or suspended in an ether or an inert hydrocarbon or a mixture of both. Diethyl ether, tetrahydrofuran and dimethoxyethane are particularly suitable. The reaction is preferably carried out at temperatures between 0° and 100° C.

The conversion according to the invention of compounds of the general formula (I) into (S)-ketoprofen is carried out by conventional methods according to the nature of the substituents R$^1$ and R$^2$ which can be varied. The oxidation methods below may be mentioned as examples:

For the direct oxidation of the ethers of secondary benzyl alcohols to give ketones, examples which may be mentioned are: nitronium tetrafluoroborate, sodium bromate/(NH$_4$)$_2$Ce(IV) (NO$_3$)$_6$, IF$_5$, UF$_6$, trityl tetrafluoroborate, chromyl chloride.

The alkyl ethers (R$^1$=OR$^3$, R$^2$=H) are preferably oxidised according to the invention without racemisation by heating in an inert solvent, such as, for example, carbon tetrachloride, with 1–2 equivalents, preferably with 1.05 to 1.2 equivalents of N-bromo-succinimide or N-chloro-succinimide, preferably with N-bromo-succinimide with addition of the conventional radical chain initiators such as benzoyl peroxide or azo-bis-isobutyronitrile or with exposure to light, preferably using benzoyl peroxide or with exposure to light.

Oxidation using sodium bromate/(NH$_4$)$_2$Ce(IV) (NO$_3$)$_6$ is likewise suitable.

Alternatively, using an ether cleavage known from the literature, the alcohol (R$^1$CR$^2$=HCOH) can first be prepared which is then further oxidised according to the process described below to give ketoprofen.

Alternatively, in a conventional process from the literature, the compound can be hydrogenolytically (for example Pd/C; H$_2$) reduced to give the benzyl group ($R^1CR^2$=HCH) which is then oxidised according to the process described below to give ketoprofen.

The methylene compound ($R^1$, $R^2$=H) can be oxidised using $KMnO_4$ and a catalyst, for example Co-naphthenate or other transition metal salts or using $O_2$/Co-naphthenate, to give ketoprofen (I).

Oxidation using $CrO_3$ in glacial acetic acid at 10° to 50° C. is likewise suitable.

For the racemisation-free oxidation of the alcohol ($R^1$=OH, $R^2$=H) to give (S)-ketoprofen (I), known oxidants such as Cr (VI) salts, selenium dioxide, bromine, sodium bromate/$(NH_4)_2Ce(IV)$ $(NO_3)_6$, are used, preferably bromine.

The oxidation is preferably carried out at room temperature in a chlorinated hydrocarbon or in an alcohol, preferably in methanol using 1-10 equivalents of bromine, preferably using 1.5-3 equivalents.

Ketals of general formula II ($R^1$, $R^2$=—O—$CH_2$—$(CH_2)_n$O—)n =1,2 can be converted according to conventional processes using sulphonic acids or aqueous mineral acid to ketoprofen (I) without racemisation.

Esters ($R^1$=H, $R^2$=OOCR³) can be converted to the alcohols according to conventional processes.

Tetrahydropyryl ethers and silyl ethers ($R^2$=$Me_3SiO$, $R^2$=H) can be converted to the alcohols according to conventional processes.

Alternatively to the abovementioned methods, benzyl ethers ($R^1$=$O_2CR^3$, $R^2$=H) or ethers ($R^1$=$OR^9$, $R^2$=H) can be hydrogenolytically converted Volume (Houben-Weyl, 4/1 c, p 400-401) to the benzyl compound ($R^1$=H, $R^2$=H), which can be converted to ketoprofen according to the above-described methods.

In the simple transfer of the asymmetric hydrogenation of naproxen, which is described in DE-A 0 272 787, to the reaction of dehydroketoprofen to give ketoprofen, a very poor enantiomeric excess of only 47% e.e. has surprisingly been found. It is therefore extremely surprising that the compounds of the formula (II) can be hydrogenated with such good enantioselectivities.

The process according to the invention permits preparation on an industrial scale of relatively large amounts of the compound (S)-ketoprofen, which is difficult to obtain according to hitherto-known processes.

The (S)-ketoprofen prepared by the process according to the invention is used as an analgesic and antipyretic (EP-A 49 62 124). In this case, the pure (S)-enantiomer has improved properties compared to the racemate.

The preparation of (S)-ketoprofen is supported by Examples 1, 2 and 3.

The preparation of the compounds of the general formula (I) is supported by Examples 4, 5, and 6.

The preparation of compounds of the general formula (II) is supported by Examples 7, 8, 9 and 10.

The preparation of compounds of the formula (III) is supported by Examples 11, 12 and 13.

The preparation of compounds of the formula (IV) is supported by Examples 14, 15 and 16.

If not expressly stated otherwise, the abbreviation BINAP represents the formula

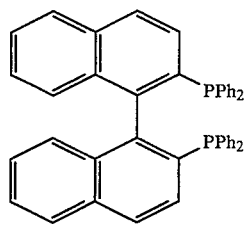

The term enantiomeric excess is defined as below; the data are reported in %:

$$e.e. = \frac{\text{Mass of the enantiomer } A - \text{mass of the enantiomer } B}{\text{Mass of the enantiomer } A + \text{mass of the enantiomer } B} \times 100$$

Determination of the enantiomeric excess was carried out by methods known from the literature (EP-A-O-379 917) by HPLC on chiral phases.

Comparison Example

Asymmetric hydrogenation of 2-((3-benzoyl)-phenyl)-propenoic acid (dehydroketoprofen)

A solution of 0.3 g (1.2 mmol) of 2-((3-benzoyl)-phenyl)-propenoic acid (Gazz. Chim. Ital. 110, 123 (1980)) in 5 ml of oxygen-free methanol and 10 mg (0.012 mmol) of Ru(S)-BINAP-$(O_2CCH_3)_2$ (EP-A 0 245 959) was poured into a 100-ml autoclave under a protective gas. After reaction for 48 h under 100 atm of hydrogen, the solvent was removed, the residue was taken up in ethyl acetate and the mixture was filtered on silica gel to remove the catalyst.

Yield: 0. 287 g (95%).

Enantiomeric excess: 47% e.e. $^1$H-NMR (250 MHz, $CDCl_3$)δ=(ppm) 1.58 (d, J=7.5 Hz; 3H, $CH_3$) 3.85 (q, J=7 Hz; 1H, $CHCH_3$), 7.4–7.95 (m; 9H, $H_{aromat.}$).

EXAMPLE 1

Oxidation of 2-(3-benzyl-phenyl)-propenoic acid 1 g (4.16 mmol) of the product from Example 4 and 2.5 g of potassium permanganate are dissolved in a mixture of 80 ml of water and 20 ml of 1N NaOH and stirred for 6 h at room temperature. Subsequently, the mixture is acidified using 4 ml of concentrated sulphuric acid and is stirred for 10 min with 40 ml of saturated sodium sulphite solution. The mixture is filtered, and the filtrate is extracted 5 times with methylene chloride. The combined organic extracts are dried and freed from the solvent. The residue taken up in ether is extracted with 1N NaOH. The aqueous phase is acidified to pH 2 using 1N HCl and extracted with methylene chloride. After drying there remain 0.54 g (51%) of (S)-ketoprofen.

Enantiomeric excess: 80% e.e.

EXAMPLE 2

Oxidation of 2-(S)-(3-methoxy-phenyl-methyl)-phenyl)-propionic acid

A solution of 3.00 g (11.1 mmol) of the product from Example 5 in 45 ml of carbon tetrachloride is refluxed together with 2.2 g (12.2 mmol) of N-bromo-succinimide and a spatula tip of dibenzoyl peroxide. After 3.5 h the cooled solution is filtered, the filtrate is freed from solvent and the residue is dissolved in ethyl acetate. The organic phase is extracted three times with 1N NaOH. The combined, acidified aqueous phases are extracted twice with ethyl acetate. The combined organic phases are dried using saturated sodium chloride solution and magnesium sulphate and concentrated by rotary evaporation. Yield 2.59 g (91%) of (S)-ketoprofen. Enantiomeric excess: 92% e.e.

EXAMPLE 3

Oxidation of 2-(3-(hydroxy-phenyl-methyl)-phenyl)-propenoic acid 6 ml of a 1M solution of bromine (6 mmol) in methanol are added to 1.00 g (3.9 mmol) of the product of Example 6 in 5 ml of methanol and the mixture is stirred at room temperature until the starting material has completely reacted (approximately 4h). Subsequently, the reaction solution is treated with ice water and 0.948 g (6 mmol) of sodium thiosulphate and concentrated on a rotary evaporator. By extraction of the aqueous residue with ethyl acetate, drying of the organic phase and column chromatography on silica gel, 0.694 mg (70%) of (S)-ketoprofen is obtained. Enantiomeric excess: 84% e.e.

EXAMPLE 4A

Asymmetric hydrogenation of 2-(3-benzyl-phenyl)-propenoic acid

A solution of 0.440 g (1.64 mmol) of 2-(3-benzyl-phenyl)-propenoic acid (product from Example 7 or 8) in 5 ml of oxygen-free methanol and 10 mg (0.0 12 mmol) of Ru-((S)-BINAP-$O_2CCH_3$)$_2$) is poured into a 100-ml autoclave under a protective gas. After 48 h of reaction under 100 atm of hydrogen, the solvent is removed, the residue is taken up in ethyl-acetate and is filtered on silica gel to remove the catalyst. Yield 0.42 g (95%). Enantiomeric excess: 80% e.e.

$^1$H-NMR (250 MHz, CDCl$_3$) δ=(ppm) 1.42 (d, J=7 Hz; 3H, CH$_3$), 3.62 (q, J=7.5 Hz; 1H, CHCH$_3$), 3.90 (s; 2H, CH$_2$), 7.1–7.3 (m; 9H, H$_{aromat.}$).

EXAMPLE 4B (Embodiment Variant)

The reaction was carried out analogously to Example 4a, but 10 mg of [(p—(CH$_3$)$_2$CH—C$_6$H$_4$—CH$_3$)Ru(S)-BINAP I]+I−(0.0090 mmol) (EP-A 366 390) was used as a catalyst.

Yield: 0.425 g (96%) Enantiomeric excess: 85% e.e.

EXAMPLE 4c (Embodiment Variant)

7.8 mg (0.011 mmol) of (S)-BINAP and 3.57 mg (0.011 mmol) of [(p—(CH$_3$)$_2$CH—C$_6$H$_4$—CH$_3$)RuCl$_2$] in 3 ml of DMF were heated to 100° C. for 10 min, and subsequently the solvent was removed in a pump vacuum. The residue was used as a catalyst as described in Example 4a.

Yield: 0.42 g (95%) Enantiomeric excess: 80% e.e.

EXAMPLE 5

Asymmetric hydrogenation of 2-(3-(methoxy-phenyl-methyl)-phenyl)-propenoic acid

The product from Example 10 was reacted analogously to Example 4. From 0.44 g of starting material, 0.42 g (94%) of 2-(S)-(3-(methoxy-phenyl-methyl)-phenyl-propionic acid was obtained.

The analysis of the enantiomers was carried out at the ketoprofen stage (see Example 2)

$^1$H-NMR (250 MHz, CDCl$_3$) δ=(ppm) 1.48 (2xd, J=7 Hz; 3H, CH$_3$), 3.38 (s; OCH$_3$), 3.72 (q, J=7.5 Hz; CHCH$_3$), 5.21 (s; 1H, HCCH$_3$), 7.1–7.4 (m; 9H, H$_{aromat.}$).

EXAMPLE 6

Asymmetric hydrogenation of 2-(3-(hydroxy-phenyl-methyl)-phenyl)-propenoic acid

The product from Example 9 was reacted analogously to Example 4. From 0.44 g of starting material, 0.42 g (94%) of 2-(S)-(3-(hydroxy-phenyl-methyl)-phenyl)-propionic acid was obtained.

Analysis of the enantiomers was carried out at the ketoprofen stage (see Example 3).

$^1$H-NMR (250 MHz, CDCl$_3$) δ=(ppm) 1.49 (d, J=7 Hz; 3H, CH$_3$), 3.73 (q, J=7.5 Hz; 1H, CHCH$_3$), 5.81 (s; 1H, HOCH), 7.1–7.4 (m; 9H, H$_{aromat.}$).

EXAMPLE 7

Preparation of 2-(3-benzyl-phenyl)-propenoic acid 136 g (0.531 mol) of 2-hydroxy-2-(3-benzyl-phenyl)-propanoic acid (product from Example 11) are refluxed in a mixture of 3 l of dioxane and 180 ml of concentrated sulphuric acid. Water is added to the mixture which has been concentrated to approximately 500 ml and the mixture is extracted three times with ether. After drying the organic phases using saturated NaCl and magnesium sulphate, a brown oil remains, which is purified by filtration on 1 kg of silica gel (ethyl acetate/cyclohexane 5:1). Yield: 83 g (66%).

$^1$H-NMR (250 MHz, CDCl$_3$) δ=(ppm) 3.99 (s; 2H, ArCH$_2$Ar), 5.95 (d; 1H, C=CH$_2$), 6.47 (d; 1H, C=CH$_2$), 7.1–7.5 (m; 9H, H-aromat.) .

GC/MS/CI (isobutane) m/z=239 (100%, M++1), 238 (80%, M+), 161 (90%, m+—C$_6$H$_5$), 91 (80%, CH$_2$Ph+).

EXAMPLE 8

Preparation of 2-(3-benzyl-phenyl)-propenoic acid A mixture of 3.48 g (13.80 mmol) of methyl 2-(3-benzyl-phenyl)-propenoate (product from Example 14a) in 2.70 g of lithium hydroxide, 25 ml of water, 27 ml of acetonitrile and 27 ml of heptane is treated overnight with intensive stirring using a mechanic stirrer. The acetonitrile/water phase is then separated and concentrated. The resulting residue is taken up in ethyl acetate and is extracted with sodium hydroxide solution. The basic extract is acidified using hydrochloric acid and is extracted with ethyl acetate, dried and concentrated.

Yield: 1.87 g (8.00 mmol) (57.0% of theory)

The spectroscopic data are identical to those of the compound from Example 7.

EXAMPLE 9

Preparation of 2-(3-(hydroxy-phenyl-methyl)-phenyl)-propenoic acid

A mixture of 2.40 g (8.96 mmol) of methyl 2-(3-(hydroxy-phenyl-methyl)-phenyl)-propenoate (product from Example 15a) in 1.76 g of lithium hydroxide, 16 ml of water, 18 ml of acetonitrile and 18 ml of heptane is treated overnight with intensive stirring using a mechanic stirrer. The acetonitrile/water phase is then separated and concentrated. The resulting residue is taken up in ethyl acetate and extracted with sodium hydroxide solution. The basic extract is acidified using hydrochloric acid and extracted with ethyl acetate, dried and concentrated. Yield: 1.87 g (7.36 mmol) (82.1% of theory)

EXAMPLE 10

Preparation of 2-(3-(methoxyphenyl-methyl)-phenyl)-propenoic acid

A mixture of 97.26 g (345.00 mmol) of methyl 2-(3-(methoxy-phenyl-methyl)-phenyl)-propenoate (product from Example 16a) in 67.00 g of lithium hydroxide, 620 ml of water, 670 ml of acetonitrile and 670 ml of heptane was treated for 3 days with intensive stirring using a mechanic stirrer. The acetonitrile/water phase was then separated and concentrated. The resulting residue was taken up in ethyl acetate and extracted with sodium hydroxide solution. The basic extract is acidified using hydrochloric acid and extracted with ethyl acetate, dried and concentrated.

Yield: 45.99 g (171.60 mmol) (49.7% of theory)

$^1$H-NMR: (CDCl$_3$, 200 MHz) δ=3.38 (s, 3H; —OCH$_3$), (5.26 (s, 1H; —CH), 5.96 (s, 1H; =CH$_2$), 6.48 (s, 1H; =CH$_2$), 7.15–7.46 (m, 9H; aromat. H), 11.47 (s, br, 1H; —COOH)

MS-CI: (isobutane, 70 eV) m/e =269 (10%, M+H+), 237 (100%), 211 (65%), 191 (10%), 121 (10%)

EXAMPLE 11

Preparation of 2-hydroxy-2-(3-benzyl-phenyl)-propanoic acid by the pyruvate process 15 g (60.7 mmol) of 3-benzyl-bromobenzene (J. Chem. Soc. 1961, 1405) in 30 ml of THF are added dropwise to 1.62 g (67.5 mmol) of magnesium in 90 ml of THF at such a rate that the mixture boils vigorously, and the mixture is boiled for a further 2 h. The cooled solution is added dropwise to a suspension of 6.68 g (71 mmol) of sodium pyruvate at 0° C. in 20 ml of THF and it is stirred for a further 1 h at this temperature and 2 h under reflux. After addition of 1N HCl, the mixture is concentrated to a great extent and ethyl acetate is added. The organic phase is separated off and extracted twice with 1N NaOH. The combined aqueous solutions are adjusted to pH 2 using concentrated HCl and are extracted twice with ethyl acetate. After drying the organic phase using saturated sodium chloride solution and magnesium sulphate, the solvent is distilled off and 12.5 g (81%) of the title product remain.

$^1$H-NMR (250 MHz, CDCl$_3$) δ=(ppm) 1.81 (s; 3H, CCH$_3$), 40.1 (s; 3H, ArCH$_2$Ar), 7.1–7.5 (m; 9H, H$_{aromat.}$).

MS/CI (isobutane) m/z=257 (5%, M+ +1) , 239 (100%, 257—H$_2$O), 211 (60%, 257—CO—H$_2$O).

EXAMPLE 12a

Preparation of 2-hydroxy-2-(3-(methoxy-phenyl-methyl)-phenyl)-propanoic acid by the pyruvate process 30 g (108 mmol) of 3-bromo-diphenyl-methoxymethane (product from Example 16d) in 60 ml of THF are added dropwise to 3.14 g (0.131 mmol) of magnesium in 200 ml of THF at such a rate that the mixture boils vigorously, and the mixture is boiled for a further 2 h. The cooled solution is added dropwise to a suspension of 21 g (190 mmol) of sodium pyruvate at 0° C. and it is stirred for a further 24 h at 50° C. After addition of ammonium chloride solution, the mixture is concentrated to a great extent and ethyl acetate is added. The organic phase is separated off and extracted twice with 1N NaOH. The combined aqueous solutions are adjusted to pH 2 using concentrated HCl and are extracted twice with ethyl acetate. After drying the organic phase using saturated sodium chloride solution and magnesium sulphate, the solvent is distilled off and 27.5 g (88.7%) of the title product remain.

$^1$H-NMR (250 MHz, CDCl$_3$) δ=(ppm) 1.77 (s; 3H, C—CH$_3$), 3.36 (s; 3H, OCH$_3$), 5.26 (s; 1H, ArCH$_2$Ar), 7.2–7.7 (m; 9H, H—Ar).

MS/CI (isobutane) m/z=269 (50%, M+ +1-H$_2$O), 255 (100%, M+ +1-OCH$_3$), 241 (40%, 255-CO).

EXAMPLE 12

(Alternative Process)

Preparation of 2-hydroxy-2-(3-(methoxy-phenyl-methyl)-phenyl)-propanoic acid by the pyruvate process/ZnCl$_2$ 2.77 g (10.0 mmol) of 3-bromo-diphenyl-methoxymethane (product from Example 16d) in 60 ml of THF are added dropwise to 0.290 g (11.9 mmol) of magnesium in 15 ml of THF at such a rate that the mixture boils vigorously, and the mixture is boiled for a further 2 h. The cooled solution is decanted off and stirred at room temperature with 0.68 g (4.99 mmol) of dry zinc (II) chloride. The reaction mixture is added dropwise to a suspension of 1.1 g (10.0 mmol) of sodium pyruvate in 200 ml of THF at 0° C., and it is stirred for a further 24 h at 50° C. After addition of ammonium chloride solution, the mixture is concentrated to a great extent and ethyl acetate is added. The organic phase is separated off and extracted twice with 1N NaOH. The combined aqueous solutions are adjusted to pH 2 using concentrated HCl and are extracted twice using ethyl acetate. After drying the organic phase using saturated sodium chloride solution and magnesium sulphate, the solvent is distilled off and 1.99 g (70%) of the title product remain.

EXAMPLE 13a

Preparation of 2-hydroxy-2-(3-(hydroxy-phenyl-methyl)-phenyl)-propanoic acid by the pyruvate process 3.35 g (10 mmol) of 3-bromo-diphenyl-trimethyl-siloxymethane in 10 ml of tetrahydrofuran are added dropwise to 0.228 g (9.5 mmol) of magnesium in 30 ml of THF at such a rate that the mixture boils vigorously, and the mixture is boiled for a further 2 h. The cooled solution is added to a suspension of 1.1 g (10 mmol) of sodium pyruvate at 40° C. and it is stirred for 1 h at this temperature and 24 h under reflux.

After addition of 15 ml of 1N HCl, the mixture is stirred for 1 h and concentrated to a great extent and ethyl acetate is added. The organic phase is separated off and extracted twice with 1N NaOH. The combined aqueous solutions are adjusted to pH 2 using concentrated HCl and are extracted twice with ethyl acetate. After drying the organic phase using saturated sodium chloride solution and magnesium sulphate, the solvent is distilled off and the residue is chromatographed on silica gel. Yield 1.5 g (55%) of the title product.

$^1$H-NMR (250 MHz, CDCl$_3$) δ=(ppm) 1.72 (s; 3H, CCH$_3$), 5.79 (s; 1H, HOCH.), 7.2–7.7 (m; 9H, H-aromat.).

EXAMPLE 13b

Preparation of 3-bromo-diphenyl-trimethylsiloxymethane

A solution of 50 g (0.19 mol) of 3-bromo-diphenyl-methanol, (Synth. Commun., 12, 881 (1982)), 26.8 g (0.25 mol) of trimethylsilyl chloride, 26.9 g of triethylamine, 1 g of dimethylaminopyridine in 600 ml of methylene chloride is stirred for 48 h at room temperature, extracted with 1% HCl, 1% NaHCO$_3$ and with saturated NaCl solution, and dried using MgSO$_4$. After removal of the solvent, the product is purified by fractional silica gel filtration (ethyl acetate in cyclohexane, 0–3%). Yield: 54 g (85%).

$^1$H-NMR (CDCl$_3$, 250 MHz) δ=(ppm) 0.10 (s, 9H, (CH$_3$)$_3$C), 5.7 (s, 1H, Ar$_2$CH), 7.1–7.5 (m, 9H)

GC/MS/EI (70 eV) m/z=336/334 (20% M$^+$+1), 319/321 (30%, M$^+$+1-CH$_3$), 255 (40%, M$^+$-Br), 243/245 (80%, PhCHC$_6$H$_4$Br$^+$), 165 (100%, C$_6$H$_5$CC$_6$H$_4$$^+$) 73 (90%, Si(CH$_3$)$_3$$^+$)

EXAMPLE 14a

Preparation of methyl 2-(3-benzyl-phenyl)-propenoate

A solution of 2.25 g (11.80 mmol) of 3-ethinyl-diphenyl-methane (product from Example 14b or 14d), 0.71 g of sodium iodide, 0.224 g of concentrated hydrochloric acid and 0.13 g of hydroquinone in 15 ml of methanol is subjected to 20 bar of carbon monoxide at 60° C. for 24 hours in a 0.1-1 steel autoclave. After the autoclave is depressurised, the mixture is evaporated to dryness and the residue is purified by chromatography on silica gel.

Yield: 0.48 g (1.92 mmol) (16.3% of theory)

MS-CI: 70 eV, isobutane) m/e=253 (100%, M+H$^+$), 221 (6%), 175 (8%), 91 (6%), $^1$H-NMR: (CDCl$_3$, 200 MHz) δ=3.74 (s, 3H; —OCH$_3$), 3.99 (s, 2H; —CH$_2$—), 5.85 (s, 1H; =CH$_2$), 6.33 (s, 1H; =CH$_2$), 6.85=7.35 (m, 9H; arom. H)

In addition to the product, 1.10 g (5.76 mmol) (48.9% of theory) of the starting material were recovered.

EXAMPLE 14b

Preparation of 3-ethinyl-diphenylmethane 0.97 g of potassium fluoride is added to a solution of 4.00 g (15.00 mmol) of 3-(trimethylsilylethinyl)diphenylmethane in 200 ml of ethanol and the mixture is stirred overnight at room temperature. The mixture is filtered off with suction, concentrated and purified by chromatography on silica gel (cyclohexane: ethyl acetate 50:1 v:v).

Yield: 2.25 g (11.70 mmol) (78.0% of theory).

MS-CI: (70 eV, isobutane) m/e =193 (100%, M+H$^+$), 157 (6%), 115 (35%), 91 (100%)

$^1$H-NMR: (CDCl$_3$, 200 MHz) δ=3.03 (s, 1H; ≡C—H), 3.96 (s, 2H; —CH$_2$), 7.10–7.40 (m, 9H; arom. H)

EXAMPLE 14c

Preparation of 3-(trimethylsilylethinyl)-diphenylmethane 2.22 g (22.50 mmol) of trimethylsilylacetylene are added under a protective gas to a solution of 3.70 g (15.00 mmol) of 3-bromodiphenylmethane (J. Chem. Soc. 1961, 1405), 0.119 g (1.50 mmol) of bis(triphenylphosphine)palladium dichloride, 0.158 g (24.00 mmol) of triphenylphosphine, 0.029 g (0.20 mmol) of copper (I) iodide in 20 ml of anhydrous triethylamine, and the mixture is refluxed overnight, the intensive condenser being held at a temperature of −8° C. by a refrigeration unit. The mixture is diluted with methylene chloride, filtered off from the precipitated salts with suction, washed twice with water, dried and concentrated. The crude product is purified by chromatography on silica gel (ethyl acetate: cyclohexane 1:20 v:v).

Yield: 4.05 g (15.30 mmol) (100% of theory).

MS-EI: (70 eV) m/e=264 (26%, M$^+$), 249 (100%), 124 (6%), 91 (8%)

$^1$H-NMR: (CDCl$_3$, 200 MHz) δ=0.75 (s, 9H; —Si—(CH$_3$)$_3$—), 3.96 (s, 2H; —CH$_2$—), 7.10–7.40 (m, 9H; arom. H)

EXAMPLE 14d

Preparation of 3-ethyldiphenylmethane from 3-hydroxy-3-methyl-butinyl-diphenylmethane 0.06 g of sodium hydride (80 per cent strength in white oil) is added to a solution of 2.50 g (9.54 mmol) of 3-hydroxy-3-methyl butinyl-diphenylmethane in 20 ml of toluene and the mixture is heated overnight, so that only a little toluene is distilled off. Subsequently the mixture was filtered off, taken up in methylene chloride and washed using hydrochloric acid, sodium carbonate and water. The crude product obtained after drying and concentration was purified by chromatography on silica gel in an ethyl acetate/cyclohexane (1/20 v/v) system.

Yield: 1.54 g (8.02 mmol) (84.1% of theory) Spectroscopic data see Example 14b

EXAMPLE 14e

Preparation of 3-(3-hydroxy-3-methyl-butinyl)-diphenylmethane 3.06 g (36.45 mmol) of 2-methyl-3-butin-2-ol under nitrogen at 95° C. are added to a solution of 6.00 g (24.30 mmol) of 3-bromodiphenylmethane (J. Chem. Soc. 161, 1405), 0.170 g (0.24 mmol) of bis(triphenylphosphine)-palladium dichloride, 0.25 g (9.72 mmol) of triphenylphosphine and 0.046 g (0.24 mmol) of copper (I) iodide in 25 ml of anhydrous triethylamine, and the mixture is refluxed overnight. The mixture is diluted with methylene chloride, filtered off from the precipitated salts with suction, washed twice using water, dried and concentrated. The crude product is purified by chromatography on silica gel.

Yield: 5.19 g (20.76 mmol) (85.4% of theory) MS-CI: (isobutane, 70 eV) m/e=251 (8%, M+H$^+$), 250 (18%, M$^+$), 233 (100%), 193 (12%), 173 (10%), 91 (21%).

EXAMPLE 15a

Preparation of methyl 2-(3-(methoxy-phenyl-methyl)-phenyl) propionate and methyl 2-(3-(hydroxyphenyl-methyl)-phenyl)-propionate A solution of 22.50 g (109.00 mmol) of 3-ethinyldiphenylmethanol (product from Example 15b or 15d), 6.60 g of sodium iodide, 2.12 g of concentrated hydrochloric acid and 1.19 g of hydroquinone in 132 ml of methanol is subjected to 20 bar of carbon monoxide in a 0.3-1 steel autoclave for 24 hours at 60° C. After depressurising the autoclave, the mixture is evaporated to dryness and the residue is purified by chromatography on silica gel (ethyl acetate: cyclohexane 1:50→1:1 v:v).

Methyl 2-(3-(methoxy-phenyl-methyl)-phenyl)-propionate

Yield: 3.22 g (11.41 mmol) (10.5% of theory)

$^1$H-NMR: (CDCl$_3$, 200 MHz) δ=3.77 (s, 3H; —OCH$_3$), 3.93 (s, 3H; —OCH$_3$), 5,25 (s, 1H; —CH—OCH$_3$), 7.20 to 7.57 (m, 9H; arom. H) MS-EI: (EI, 70 eV) m/e=282 (28%, M$^+$), 251 (100%), 250 (80%), 222 (20%), 205 (82%), 191 (100%), 189 (52%), 178 (12%), 165 (24%), 121 (85%), 105 (44%).

methyl 2-(3-(hydroxy-phenyl-methyl)-phenyl)-propionate

Yield: 2.50 g (9.33 mmol) 8.6% of theory) MS-EI: (EI, 70 eV) m/e=268 (28%, M$^+$), 250 (12%), 236 (22%), 208 (80%), 191 (26%), 189 (87%), 163 (84%), 131 (78%), 105 (96%), 103 (100%).

In addition to the products, 2.80 g (13.46 mmol) (12.3% of theory) of the starting material were recovered and 2.99 g of 3-bromodiphenylmethoxymethane were isolated.

EXAMPLE 15b

Preparation of 3-ethinyl-diphenylmethanol 1.44 g of potassium fluoride are added to a solution of 6.30 g (22.00 mmol) of 3-(trimethylsilylethinyl)-diphenylmethanol in 50 ml of ethanol, and the mixture is stirred overnight at room temperature. The mixture is filtered off with suction, concentrated and purified by chromatography on silica gel (cyclohexane: ethyl acetate 50:1 v:v).

Yield: 3.45 g (15.90 mmol) (72.0% of theory) MS-EI: (EI, 70 eV) m/e=208 (84%, M+), 189 (17%), 178 (12%), 129 (65%), 105 (100%), 103 (28%).

EXAMPLE 15c

Preparation of 3-(trimethylsilylethinyl)-diphenylmethanol 4.49 g (45.00 mmol) of trimethylsilylacetylene are added under nitrogen to a solution of 7.89 g (30.00 mmol) of 3-bromodiphenylmethanol (Synth. Commun. 12, 881 (1982)), 0.237 g (0.30 mmol) of bis(triphenylphosphine)palladium dichloride, 0.315 g (1.20 mmol) of triphenylphosphine, 0.057 g (0.30 mmol) of copper (I) iodide in 30 ml of anhydrous triethylamine, and the mixture is refluxed overnight, the intensive condenser being maintained at $-8°$ C. by means of a refrigeration unit. The mixture is diluted with methylene chloride, filtered off from the precipitated salts with suction, washed twice using water, dried and concentrated. The crude product is purified by chromatography on silica gel (ethyl acetate: cyclohexane 1:20 v:v).

Yield: 6.35 g (22.00 mmol) (73.0% of theory) MS-CI: (70 eV, isobutane) m/e=279 (10%, M+H+), 211 (5%), 201 (10%), 183 (5%)

$^1$H-NMR: (CDCl$_3$, 200 MHz) $\delta$=0.25 (s, 9H; —Si(CH$_3$)$_3$), 2.28 (s, 1H; —CH—OH), 5.77 (s, 1H; —CH—OH), 7.20–7.57 (m, 9H; arom. H)

EXAMPLE 15d

Preparation of 3-ethinyldiphenylmethanol from 3-(3-hydroxy-3-methyl-butinyl)-diphenylmethane 0.36 g of sodium hydride (60 per cent strength in white oil) is added to a solution of 10.00 g (35.97 mmol) in 3-(3-hydroxy-3-methyl-butinyl)-diphenylmethanol in toluene and the mixture is heated over night in such a manner that only a little toluene distils off. The mixture was then filtered off, taken up in methylene chloride and washed using sodium carbonate and water. The crude product obtained after drying and concentration was purified by chromatography on silica gel (ethyl acetate: cyclohexane 1:10 v:v).

Yield: 0.78 g (3.59 mmol) (10% of theory)

The spectroscopic data correspond to those of the compound from Example 15b.

EXAMPLE 15e

Preparation of 3-(3-hydroxy-3-methyl-butinyl)-diphenylmethanol 8.62 g (102.60 mmol) of 2-methyl-3-butin-2-ol are added under a protective gas at 95° C. to a solution of 18.00 g (68.40 mmol) of 3-bromodiphenylmethanol (Synth. Commun. 12, 881 (1982)), 0.48 g (0.68 mmol) of bis(triphenylphosphine)palladium dichloride, 0.71 g (2.70 mmol) of triphenylphosphine and 0.13 g of (0.68 mmol) of copper (I) iodide in 20 ml of anhydrous triethylamine, and the mixture is refluxed overnight. The mixture is diluted with methylene chloride, filtered off from the precipitated salts with suction, washed twice using water, dried and concentrated. The crude product is purified by chromatography on silica gel (mobile phase: ethyl acetate: cyclohexane 1:3 v:v).

Yield: 20.10 g (15.4 mmol) (quantitative) MS-CI: (isobutane, 70 eV) m/e=266 (12%, M+H+), 249 (100%), 191 (33%).

EXAMPLE 16a

Preparation of methyl 2-(3-(methoxy-phenyl-methyl)-phenyl)-propenoic acid

A solution of 104.80 g (0.472 mol) of 3-ethinyl-diphenyl-methoxymethane, 28.60 g of sodium iodide, 9.18 g of concentrated hydrochloric acid and 5.15 g of hydroquinone in 570 ml of methanol and 250 ml of toluene is subjected to 20 bar of carbon monoxide in a 1.3–1 steel autoclave for 12 hours at 60° C. After depressurising the autoclave, the mixture is evaporated to dryness and the residue is purified by chromatography on silica gel (ethyl acetate: cyclohexane 1:50→ v:v).

Yield: 27.60 g (97.87 mmol) (20.7% of theory)

The spectroscopic data correspond to those of the compound from Example 15a.

In addition to the product, 25.32 g (114.05 mmol) (24.2% of theory) of the starting material were recovered.

EXAMPLE 16b

Preparation of 3-ethinyl-diphenylmethoxymethane from 3-(3-hydroxy-3-methyl-butinyl)-diphenylmethoxymethane A suspension of 225.20 g (0.80 mol) of 3-(3-hydroxy-3-methyl-butinyl)-diphenylmethoxymethane and 32.80 g powdered sodium hydroxide in 3000 ml of anhydrous toluene is refluxed under nitrogen for 16 hours. The powdered sodium hydroxide is then filtered off with suction and the mixture is washed twice using water, dried and concentrated.

The crude product is purified by chromatography on silica gel (mobile phase: ethyl acetate: cyclohexane 1:10 v:v).

Yield: 439.68 g (1.57 mol) (83.0% of theory) $^1$H-NMR: (CDCl$_3$, 200 MHz) $\delta$=2.34 (s, 1H; ≡C—H), 3.36 (s, 3H; —OCH$_3$), 5.19 (s, 1H; —CH—), 7.10 to 7.45 (m, 9H; arom. H).

EXAMPLE 16c

Preparation of 3-(3-hydroxy-3-methyl-butinyl)-diphenylmethoxymethane 237.17 g (2.85 mol) of 2-methyl-3-butin-2-ol are added under nitrogen at 95° C. to a solution of 524.65 g (1.90 mol) of 3-bromo-diphenylmethoxymethane, 13.30 g (19.00 mmol) of bis(triphenylphosphine)palladium dichloride, 19.76 g (76.00 mmol) of triphenylphosphine and 3.59 g (19.00 mmol) of copper(I) iodide in 20 ml of anhydrous triethylamine, and the mixture is refluxed overnight. The mixture is diluted with methylene chloride, filtered off from the precipitated salts with suction, washed twice with water, dried and concentrated. The crude product is purified by chromatography on silica gel (mobile phase: ethyl acetate: cyclohexane 1:10 v:v).

Yield: 439.68 g (1.57 mol) (83.0% of theory) $^1$H-NMR: (CDCl$_3$, 200 MHz) $\delta$=1.40 (s, 6H; —CH$_3$), 2.10 (s, br, 1H; —OH), 3.37 (s, 3H; —OCH$_3$), 5.19 (s, 1H, —CH), 7.20–7.46 (m, 9H; aromat. H) MS-CI: (isobutane, 70 eV) m/e=281 (6%, M+H+), 280 (18%, M+), 263 (100%), 249 (64%), 191 (94%), 121 (40%)

EXAMPLE 16d

Preparation of 3-bromo-diphenylmethoxymethane

A total of 42.00 g of sodium hydride (80 per cent strength in white oil) is added in portions at approximately 15° C. to a solution of 272.00 g (1.03 mol) of 3-bromo-diphenylmethanol (J. Chem. Soc., 1961, 1405) in 2500 ml of anhydrous tetrahydrofuran. After hydrogen formation is complete, the mixture is stirred for 1 further hour at room temperature, and is then maintained at 50°-60° C. and 98.0 ml of methyl iodide are added dropwise. After addition is complete, the mixture is heated for a further 4 hours under reflux. 2N hydrochloric acid is then added with cooling, 1250 ml of ethyl acetate are added, and the mixture is extracted twice using water. The crude product obtained after drying and concentration is distilled. A light yellowish oil is obtained.

Yield: 165.65 g (0.59 mol) (58.1% of theory) $^1$H-NMR: (CDCl$_3$, 200 MHZ) $\delta$=3.36 (s, 3H; —OCH$_3$), 5.18 (s, 1H; —CH—), 7.10–7.55 (m, 9H; aromat. H) MS-EI: (EI, 70 eV) m/e=222 (82%, M+), 207 (26%), 191 (100%), 189 (58%), 145 (50%), 129 (24%) 121 (70%), 115 (8%), 105 (28%), 101 (14%)

We claim:

1. A (2)-arylpropenoic acid of the formula (II)

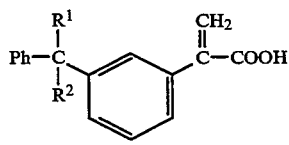
(II)

in which
Ph is a phenyl radical, and
R$^1$ and R$^2$ are identical or different and in each case represent hydrogen, hydroxyl, alkoxy having up to 10 C atoms, cycloalkoxy having 5 to 10 C atoms, aralkoxy having 7 to 12 C atoms or aryloxy having 6 to 10 C atoms, which is unsubstituted or substituted by alkyl or alkoxy having in each case 1 to 5 C atoms, or
represent the group O$_2$CR$^3$ where R$^3$ is hydrogen, alkyl having up to 10 C atoms, cycloalkyl having 5 to 10 C atoms, aralkyl having 7 to 12 C atoms or aryl having 6 to 10 C atoms and unsubstituted or substituted by alkyl or alkoxy having in each case 1 to 5 C atoms, or
represent the group OSiR$^4$R$^5$R$^6$, where R$^4$, R$^5$ and R$^6$, independently of each other, each have the meaning given for R$^3$, or
represent the group NR$^7$R$^8$, where R$^7$ and R$^8$, independently of each other, have the meaning given for R$^3$, or
represent a 2-tetrahydropyryl group, or
R$^1$ and R$^2$ together represent a group of the structure

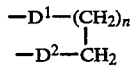

in which

D$^1$ and D$^2$, independently of each other, each represent oxygen, sulphur or the group NR$^3$, where R$^3$ has the meaning given above, and
n represents 1, 2 or 3.

2. A compound according to claim 1, in which
R$^1$ and R$^2$ are identical or different and in each case represent hydrogen, hydroxyl, alkoxy having 1 to 4 C atoms, benzyloxy, acetyloxy, benzoyloxy, tri(alkyl)silyl having in each case 1 to 4 C atoms in the alkyl radicals, dialkylamino having in each case 1 to 4 C atoms in the alkyl radicals or 2-tetrahydropyryl or
R$^1$ and R$^2$ together represent the group —O(CH$_2$-)$_n$—CH$_2$—D$^2$—, where n represents 1, 2 or 3 and D$^2$ represents oxygen or alkylamine having 1 to 4 C atoms.

3. A process for the preparation of (S)-ketonprofen which comprises hydrogenating in the presence of a catalyst which comprises a chiral transition metal complex a compound of the formula

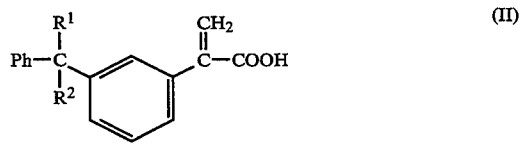
(II)

in which
Ph is a phenyl radical, and
R$^1$ and R$^2$ and identical or different and in each case represent hydrogen, hydroxyl, alkoxy having up to 10 C atoms, cycloalkoxy having 5 to 10 C atoms, aralkoxy having 7 to 12 C atoms or aryloxy having 6 to 10 C atoms, which is unsubstituted or substituted by alkyl or alkoxy having in each case 1 to 5 C atoms, or
represent the group O$_2$CR$^3$, where R$^3$ is hydrogen, alkyl having up to 10 C atoms, cycloalkyl having 5 to 10 C atoms, aralkyl having 7 and 12 C atoms or aryl having 6 to 10 C atoms and unsubstituted or substituted by alkyl or alkoxy having in each case 1 to 5 C atoms, or
represent the group OSiR$^4$R$^5$R$^6$, where R$^4$, R$^5$ and R$^6$, independently of each other, each have the meaning given for R$^3$, or
represent the group NR$^7$R$^8$, and R$^7$ and R$^8$, independently of each other, have the meaning given for R$^3$, or
represent a 2-tetrahydropyryl group, or
R$^1$ and R$^2$ together represent a group of the structure

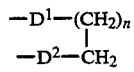

in which
D$^1$ and D$^2$, independently or each other, each represent oxygen, sulphur or the group NR$^3$, where R$^3$ has the meaning given above, and
n represents 1,2 or 3,
but R$^1$ and R$^2$ do not simultaneously represent hydrogen, thereby to produce an intermediate of the formula

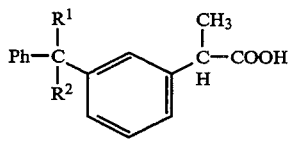

(I)

and oxidizing the $CR^1R^2$ group into a keto group.

4. A compound of the formula

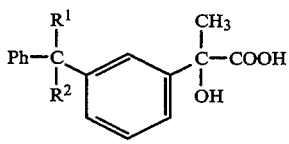

(III)

in which

Ph is a phenyl radical, and $R^1$ and $R^2$ are identical or different and in each case represent hydrogen, hydroxyl, alkoxy having up to 10 C atoms, cycloalkoxy having 5 to 10 C atoms, aralkoxy having 7 to 12 C atoms or aryloxy having 6 to 10 C atoms, which is unsubstituted or substituted by alkyl or alkoxy having in each case 1 to 5 C atoms, or represent the group $O_2CR^3$, where $R^3$ is hydrogen, alkyl having up to 10 C atoms, cycloalkyl having 5 to 10 C atoms, aralkyl having 7 to 12 C atoms or aryl having 6 to 10 C atoms and unsubstituted or substituted by alkyl or alkoxy having in each case 1 to 5 atoms, or represent the group $OSiR^4R^5R^6$, where $R^4$, $R^5$ and $R^6$, independently of each other, each have the meaning given for $R^3$, or represent the group $NR^7R^8$, where $R^7$ and $R^8$, independently of each other, have the meaning given for $R^3$, or represent a 2-tetrahydropyryl group, or $R^1$ and $R^2$ together represent a group of the structure

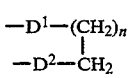

in which $D^1$ and $D^2$, independently of each other, each represent oxygen, sulphur or the group $NR^3$, where $R^3$ has the meaning given above, and n represent 1, 2 or 3, but $R^1$ and $R^2$ do not simultaneously represent hydrogen.

5. A compound of the formula

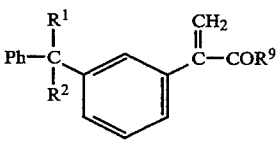

(IV)

in which

Ph is a phenyl radical, and $R^1$ and $R^2$ are identical or different and in each case represent hydrogen, hydroxyl, alkoxy having up to 10 C atoms, cycloalkoxy having 5 to 10 C atoms, aralkoxy having 7 to 12 C atoms or aryloxy having 6 to 10 C atoms, which is unsubstituted or substituted by alkyl or alkoxy having in each case 1 to 5 C atoms, or represent the group $O_2CR^3$, where $R^3$ is hydrogen alkyl having up to 10 C atoms, cycloalkyl having 5 to 10 C atoms, aralkyl having 7 to 12 C atoms or aryl having 6 to 10 C atoms and unsubstituted or substituted by alkyl or alkoxy having in each case 1 to 5 C atoms, or represent the group $OSiR^4R^5R^6$, where $R^4$, $R^5$ and $R^6$, independently or each other, each have the meaning given for $R^3$, or represent the group $NR^7R^8$, where $R^7$ and $R^8$, independently of each other, have the meaning given for $R^3$, or represent a 2-tetrahydropyryl group, or $R^1$ and $R^2$ together represent a group of the structure

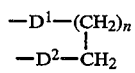

in which $D^1$ and $D^2$, independently of each other, each represent oxygen, sulphur or the group $NR^3$, where $R^3$ has the meaning given above, and n represents 1, 2 and 3, but $R^1$ and $R^2$ do not simultaneously represent hydrogen.

6. A process for the preparation of a compound according to claim 5, which comprises reacting a compound of the formula

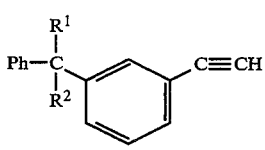

(V)

with carbon monoxide in the presence of palladium on charcoal as catalyst at a pressure 1 and 200 bar with an alcohol and with addition of mineral acid at a temperature between 25° and 160° C.

7. A process for the preparation of a compound of the formula

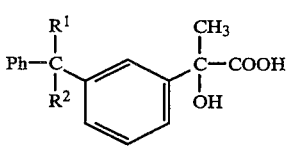

(III)

in which

Ph is a phenyl radical, and $R^1$ and $R^2$ are identical or different and in each case represent hydrogen, hydroxyl, alkoxy having up to 10 C atoms, cycloalkoxy having 5 to 10 C atoms, aralkoxy having 7 to 12 C atoms or aryloxy having 6 to 10 C atoms, which is unsubstituted or substituted by alkyl or alkoxy having in each case 1 to 5 atoms, or represent the group $O_2CR^3$, where $R^3$ is hydrogen alkyl having up to 10 C atoms, cycloalkyl having 5 to 10 C atoms, aralkyl having 7 to 12 C atoms or aryl having 6 to 10 C atoms and unsubstituted or substituted by alkyl or alkoxy having in each case 1 to 5 C atoms, or represent the group OSiR$^4$R$^5$R$^6$, where R$^4$, R$^5$ and R$^6$, independently of each other, each have the meaning given for R$^3$, or represent the group NR$^7$R$^8$, where R$^7$ and R$^8$, independently of each other, have the meaning given for R$^3$, or represent a 2-tetrahydropyryl group, or R$^1$ and R$^2$ together represent a group of the structure

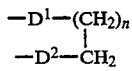

in which
D$^1$ and D$^2$, independently of each other, each represent oxygen, sulphur or the group NR$^3$, where R$^3$ has the meaning given above, and
n represents 1,2 or 3, which comprises reacting Grignard compound of the formula

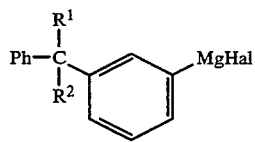

(VI)

in which
Hal represents fluorine, iodine, chlorine or bromine, with a metal pyruvate of the formula

(VII)

in which
Me represents an alkali metal, a half equivalent of an alkaline earth metal or MgBr,
in the presence of an organic solvent at a temperature between $-10°$ C. and $+120°$ C.

* * * * *

UNITED STATES PATENT AND TRADEMARK OFFICE
CERTIFICATE OF CORRECTION

PATENT NO. : 5,362,907
DATED : November 8, 1994
INVENTOR(S) : Christian Laue, et al.

It is certified that error appears in the above-identified patent and that said Letters Patent is hereby corrected as shown below:

Column 18, line 18, delete "(S)-ketonprofen" and substitute --(S)-ketoprofen--

Column 18, line 66, delete "but $R^1$ and $R^2$ do not simultaneously represent hydrogen,"

Column 19, line 8, after "keto group" insert --by oxidation in known manner--

Column 20, line 4, after "hydrogen" insert a --,-- (comma)

Column 20, line 43, after "pressure" insert --between--

Column 20, line 65, after "hydrogen" insert a --,-- (comma)

Signed and Sealed this

Thirteenth Day of April, 1999

*Attest:*

Q. TODD DICKINSON

*Attesting Officer*        *Acting Commissioner of Patents and Trademarks*